US008109127B2

(12) United States Patent
Gysling et al.

(10) Patent No.: US 8,109,127 B2
(45) Date of Patent: *Feb. 7, 2012

(54) MEASUREMENT OF ENTRAINED AND DISSOLVED GASES IN PROCESS FLOW LINES

(75) Inventors: Daniel L. Gysling, Glastonbury, CT (US); Douglas H. Loose, Southington, CT (US)

(73) Assignee: CiDRA Corporate Services, Inc., Wallingford, CT (US)

( * ) Notice: Subject to any disclaimer, the term of this patent is extended or adjusted under 35 U.S.C. 154(b) by 62 days.

This patent is subject to a terminal disclaimer.

(21) Appl. No.: 12/494,956

(22) Filed: Jun. 30, 2009

(65) Prior Publication Data
US 2010/0107727 A1    May 6, 2010

Related U.S. Application Data

(60) Continuation of application No. 12/040,385, filed on Feb. 29, 2008, now Pat. No. 7,571,633, which is a division of application No. 11/500,073, filed on Aug. 7, 2006, now abandoned, which is a continuation of application No. 10/762,409, filed on Jan. 21, 2004, now Pat. No. 7,086,278.

(60) Provisional application No. 60/482,516, filed on Jun. 24, 2003, provisional application No. 60/441,652, filed on Jan. 22, 2003, provisional application No. 60/441,395, filed on Jan. 21, 2003.

(51) Int. Cl.
*G01N 29/024* (2006.01)

(52) U.S. Cl. ....... 73/19.03; 73/19.1; 73/61.41; 73/61.79

(58) Field of Classification Search ................. 73/19.01, 73/19.03, 19.1, 61.41, 61.79; 702/50
See application file for complete search history.

(56) References Cited

U.S. PATENT DOCUMENTS
4,048,853 A    9/1977 Smith et al.
(Continued)

FOREIGN PATENT DOCUMENTS
EP    0484876    5/1992
(Continued)

OTHER PUBLICATIONS

Gibson, R.L. et al., "Viscous Attenuation of Acoustic Waves in Suspensions", J. Acoust. Soc. Am., vol. 65, No. 5, Mat 1989, pp. 1925-1934.*

(Continued)

*Primary Examiner* — Daniel Larkin (57) ABSTRACT

A device for measurement of entrained and dissolved gas has a first module arranged in relation to a process line for providing a first signal containing information about a sensed entrained air/gas in a fluid or process mixture flowing in the process line at a process line pressure. The device features a combination of a bleed line, a second module and a third module. The bleed line is coupled to the process line for bleeding a portion of the fluid or process mixture from the process line at a bleed line pressure that is lower than the process pressure. The second module is arranged in relation to the bleed line, for providing a second signal containing information about a sensed bleed line entrained air/gas in the fluid or process mixture flowing in the bleed line. The third module responds to the first signal and the second signal, for providing a third signal containing information about a dissolved air/gas flowing in the process line based on a difference between the sensed entrained air/gas and the sensed bleed line entrained air/gas.

7 Claims, 7 Drawing Sheets

U.S. PATENT DOCUMENTS

| | | | |
|---|---|---|---|
| 4,080,837 A | 3/1978 | Alexander et al. | |
| 4,248,085 A | 2/1981 | Coulthard | |
| 4,445,389 A | 5/1984 | Potzick et al. | |
| 4,896,540 A | 1/1990 | Shakkottai et al. | |
| 5,040,415 A | 8/1991 | Barkhoudarian | |
| 5,083,452 A | 1/1992 | Hope | |
| 5,218,197 A | 6/1993 | Carroll | |
| 5,285,675 A | 2/1994 | Colgate et al. | |
| 5,295,083 A | 3/1994 | Yano et al. | |
| 5,367,911 A | 11/1994 | Jewell et al. | |
| 5,398,542 A | 3/1995 | Vasbinder | |
| 5,524,475 A | 6/1996 | Kolpak et al. | |
| 5,526,844 A | 6/1996 | Kamen et al. | |
| 5,589,642 A | 12/1996 | Agar et al. | |
| 5,591,922 A | 1/1997 | Segeral et al. | |
| 5,602,348 A | 2/1997 | Takakarhu et al. | |
| 5,741,980 A | 4/1998 | Hill et al. | |
| 5,770,805 A | 6/1998 | Castel | |
| 5,770,806 A | 6/1998 | Hiismaki | |
| 5,835,884 A | 11/1998 | Brown | |
| 5,845,033 A | 12/1998 | Berthold et al. | |
| 5,948,959 A | 9/1999 | Peloquin | |
| 6,016,702 A | 1/2000 | Maron | |
| 6,151,958 A | 11/2000 | Letton et al. | |
| 6,202,494 B1 | 3/2001 | Riebel et al. | |
| 6,354,147 B1 | 3/2002 | Gysling et al. | |
| 6,378,357 B1 | 4/2002 | Han et al. | |
| 6,435,030 B1 | 8/2002 | Gysling et al. | |
| 6,463,813 B1 | 10/2002 | Gysling | |
| 6,536,291 B1 | 3/2003 | Gysling et al. | |
| 6,550,342 B2 | 4/2003 | Croteau et al. | |
| 6,587,798 B2 | 7/2003 | Kersey et al. | |
| 6,601,458 B1 | 8/2003 | Gysling et al. | |
| 6,609,069 B2 | 8/2003 | Gysling | |
| 6,691,584 B2 | 2/2004 | Gysling et al. | |
| 6,732,575 B2 | 5/2004 | Gysling et al. | |
| 6,782,150 B2 | 8/2004 | Davis et al. | |
| 6,813,962 B2 | 11/2004 | Gysling et al. | |
| 6,837,098 B2 | 1/2005 | Gysling et al. | |
| 7,086,278 B2 * | 8/2006 | Gysling et al. | 73/61.41 |
| 7,571,633 B2 * | 8/2009 | Gysling et al. | 73/19.03 |
| 7,617,716 B2 * | 11/2009 | Gysling et al. | 73/19.03 |
| 2002/0123852 A1 | 9/2002 | Gysling et al. | |
| 2002/0129662 A1 | 9/2002 | Gysling et al. | |
| 2003/0136186 A1 | 7/2003 | Gysling et al. | |
| 2003/0154036 A1 | 8/2003 | Gysling et al. | |
| 2004/0016284 A1 | 1/2004 | Gysling et al. | |

FOREIGN PATENT DOCUMENTS

| | | |
|---|---|---|
| WO | WO 93/14382 | 7/1993 |
| WO | WO 99/67629 | 12/1999 |
| WO | WO 0246705 | 6/2002 |

OTHER PUBLICATIONS

"Noise and Vibration Control Engineering Principles and Applications", Leo L. Beranek and Istvan L. Ver, A. Wiley Interscience Publication, pp. 537-541, Aug. 1992.

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, pp. 27-35.

* cited by examiner

MEASUREMENT OF ENTRAINED AND DISSOLVED GASES IN PROCESS FLOW LINES

CROSS-REFERENCE TO RELATED APPLICATIONS

This application is a continuation of U.S. patent application Ser. No. 12/040,385, filed 29 Feb. 2008, now U.S. Pat. No. 7,571,633, which is a divisional application of U.S. patent application Ser. No. 11/500,073, filed on Aug. 7, 2006, now abandoned, which is a continuation of U.S. patent application Ser. No. 10/762,409, filed on Jan. 21, 2004, and now U.S. Pat. No. 7,086,278, which claimed the benefit of U.S. Provisional Patent Application No. 60/482,516, filed Jun. 24, 2003; U.S. Provisional Patent Application No. 60/441,652, filed Jan. 22, 2003; U.S. Provisional Patent Application No. 60/441,395, filed Jan. 21, 2003; all of which are incorporated herein by reference in their entirety.

BACKGROUND OF THE INVENTION

1. Technical Field

The present invention generally relates to a device for measuring dissolved air in a fluid or process mixture flowing in a process line.

2. Description of Related Art

Monitoring levels of entrained and dissolved gases is desirable in many industrial processes. For example, entrained and dissolved gases in the approach system of paper making machines are often problematic, leading to a wide variety of problems, including flow line pulsations, pin-holes in the produced paper, reduced paper sheet strength, and excessive build-up of aerobic growths.

Entrained gases are gases that exist in a gaseous form, mixed in the process fluid. For many industrial applications with small, less than ±20% gas fraction by volume, the gas is typically in the form of small bubbles contained in a liquid continuous mixture. Entrained gases exist as either free bubbles moving within the stock or as bound (or residual) air that is adhered to the fiber. In either cases, entrained air can generally be detected by monitoring the compressibility of the mixture and correlating the compressibility to volumetric percentage of entrained air.

Dissolved gases are dissolved within the mixture on a molecular level. While in the solution, dissolved gases pose few operation problems. Typically dissolved gases have a negligible effect on the compressibility of the mixture. Thus, dissolved gases are difficult to detect via compressibility measurements.

Although dissolved gases are typically not problematic while dissolved, problems arise when dissolved gases come out of a solution as a result of either decreases in pressure or increases in temperature. One example of this is in pressurized head boxes on paper machines where the pressure drop associated with spraying the pulp/water mixture on to the paper machine can cause dissolved gases to come out of the solution and form entrained air.

Thus, to accurately monitor problems associated with entrained and dissolve gases, it is desirable to be able to measure both quantities.

SUMMARY OF THE INVENTION

In its broadest sense, the present invention provides a new and unique device having a first module arranged in relation to a process line for providing a first signal containing information about a sensed entrained air/gas in a fluid or process mixture flowing in the process line at a process line pressure. The device features a combination of a bleed line, a second module and a third module. The bleed line is coupled to the process line for bleeding a portion of the fluid or process mixture from the process line at a bleed line pressure that is lower than the process pressure. The second module is arranged in relation to the bleed line, for providing a second signal containing information about a sensed bleed line entrained air/gas in the fluid or process mixture flowing in the bleed line. The third module responds to the first signal and the second signal, for providing a third signal containing information about a dissolved air/gas flowing in the process line based on a difference between the sensed entrained air/gas and the sensed bleed line entrained air/gas.

In one embodiment, the first module is a primary process line entrained air measurement module that includes an array of sensors that measures the speed of sound propagating through the fluid or process mixture flowing within the process line and determines the entrained air based on a measurement using the speed of sound. The second module is a bleed line entrained air measurement module that also includes an array of sensors that measures the speed of sound propagating through the fluid or process mixture flowing within the bleed line and determines the bleed line entrained air based on a measurement using the speed of sound. The third module is a dissolved air determination processor module that processes the first and second signals and provides the third signal containing information about a dissolved air/gas flowing in the process line.

The device also includes a bleed line control module for controlling the bleeding off of the portion of the fluid from the process line via a bleed valve and the reinjection of said portion back to the process line via a boost pump, and also includes a controller module for controlling and coordinating the operation of the first, second and third modules, as well as a bleed line control that communicates with the bleed valve and the boost pump.

In operation, the device according to the present invention measures dissolved gases at an operating pressure by measuring entrained gases present in a process line once the fluid or process mixture is expanded to ambient (or other known and relevant) pressure. This measurement is performed using a small amount of process mixture bled-off, either continuously or periodically, from the process. The bled-off process fluid can be recirculated or, via a boost pump, re-pressurized and reinjected. The bleed line and flow rates may be sized to minimize the amount of stock bleed off while maintained sufficiently high flow rates to maintain sufficiently homogenous flow within the bled-off liquid test section (i.e. minimize slip) such that the measured gas volume fraction within the bleed line is indeed representative of the amount of gas dissolved in the process fluid. Maintaining sufficiently high velocities avoids problems associated with stratification of the mixture and the problems associated with either the liquid or gas phases "holding up" in the process pipe. For most mixtures of liquids and gases at or near ambient pressures, flow velocities of several feet per second through the line are sufficient.

The process of the throttling of the process fluid to the reduced pressure provides sufficient noise to perform a sonar-based speed measurement.

The present invention also provides a method for measuring the entrained gas fraction at two relevant pressures, and thus provides practical measurement of the amount of both entrained and dissolved gases contained in the process fluid at the process operating conditions.

The foregoing and other objects, features and advantages of the present invention will become more apparent in light of the following detailed description of exemplary embodiments thereof.

BRIEF DESCRIPTION OF THE DRAWING

The drawing, not drawn to scale, includes the following Figures.

BEST MODE FOR CARRYING OUT THE INVENTION

Figure 1:
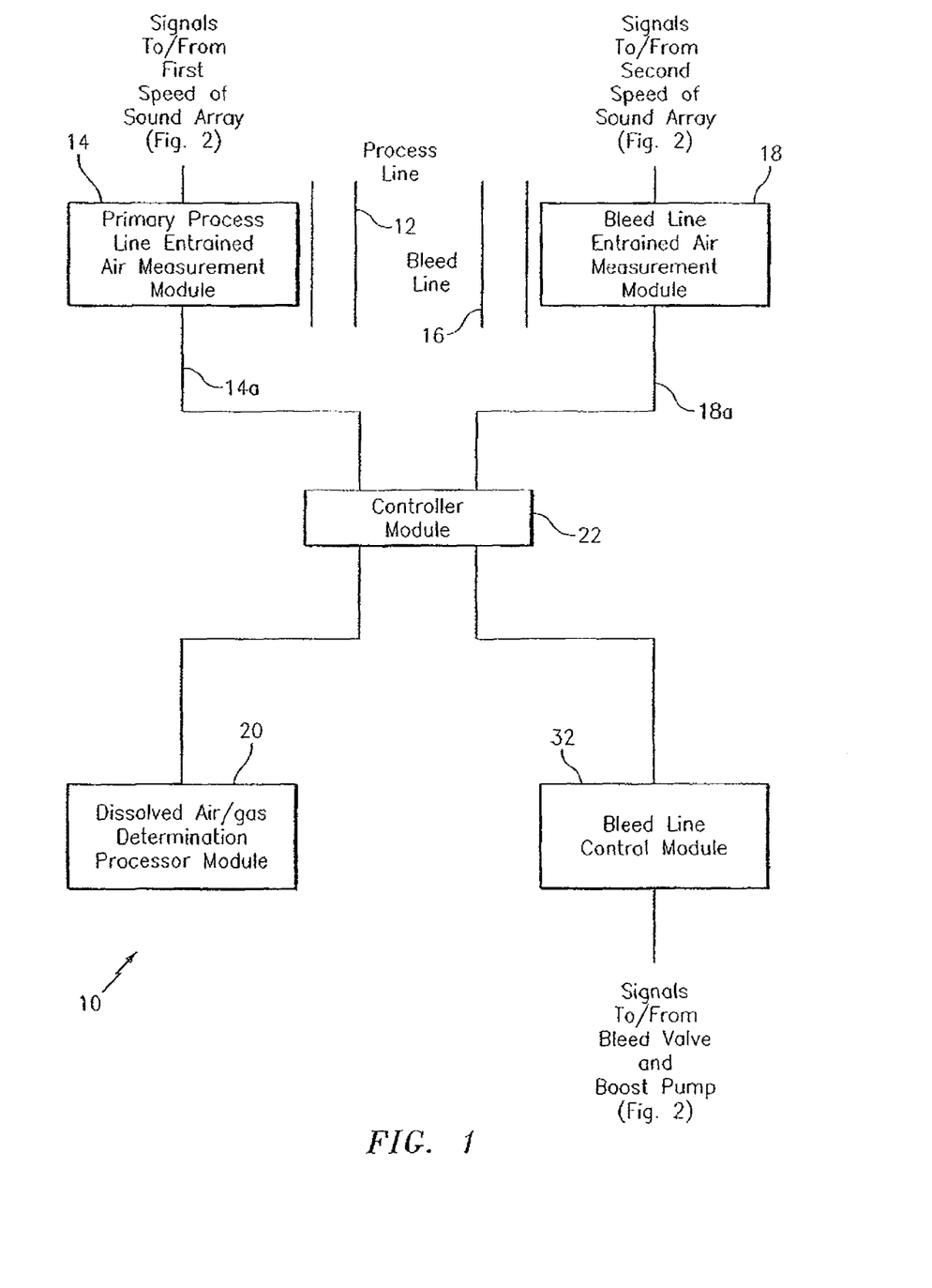
FIG. 1 is a block diagram of a device for measurement of entrained and dissolved gases that is the subject matter of the present invention.
Figure 2:
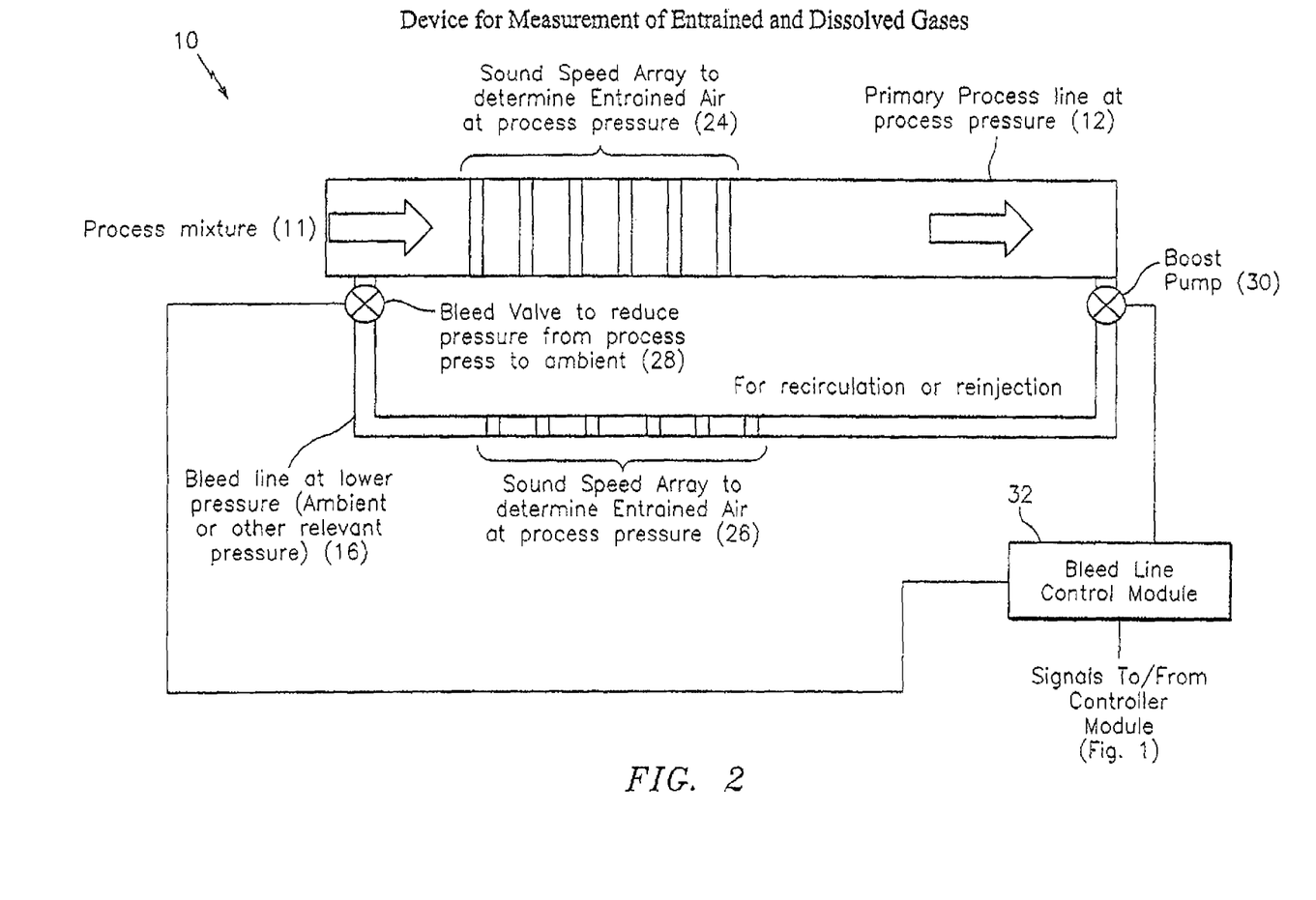
FIG. 2 is a schematic of the device shown in FIG. 1.

FIGS. 1 and 2 show a schematic and block diagram of a device generally indicated as 10 for measurement of entrained and dissolved gases in a fluid or process mixture generally indicated as 11 flowing in a primary process line 12 having a given process pressure.

In FIG. 1, the device 10 includes a first, or primary process line, entrained air measurement module 14, a bleed line 16 (see also FIG. 2), a second, or bleed line, entrained air measurement module 18 and a dissolved air/gas determination processor module 20. The primary process line entrained air measurement module 14 is arranged in relation to the primary process line 12, for sensing entrained air in the fluid or process mixture 11 and providing a first entrained air measurement module signal via line 14a containing information about sensed primary process line entrained air. As best shown in FIG. 2, the bleed line 16 is coupled to the primary process line 12 for bleeding fluid or process mixture from the primary process line 12 at a bleed line pressure that is lower than the process pressure, for example, at ambient pressure. As best shown in FIG. 1, the second entrained air measurement module 18 is arranged in relation to the bleed line 16, for sensing entrained air in the fluid or process mixture in the bleed line, and providing a second entrained air measurement module signal via line 18a containing information about sensed bleed line entrained air. In FIG. 1, the dissolved air/gas determination processor module 20 responds to the first entrained air measurement module signal along line 14a and the second entrained air measurement module signal along line 18a, each signal being received via a controller module 22 as shown and discussed below; determines dissolved air/gas in the fluid or process mixture flowing in the primary process line based on a difference between the sensed primary process line entrained air and the sensed bleed line entrained air; and provides a dissolved air/gas determination processor module signal containing information about the same.

The controller module 22 controls and coordinates the operation of the modules 14, 18, 20 and 32. As shown, the signals along lines 14a, 18a are provided directly to the controller module 22, although the scope of the invention is intended to include embodiments in which the signals along lines 14a, 18a are provided directly to the dissolved air/gas determination processor module 20. The bleed line control module 32 controls the bleed valve 28 and boost pump 30 (see FIG. 2) in response to a signal from the controller module 22.

The primary process line entrained air measurement module 14 includes an array of sensors 24 shown in FIG. 2 that measures the speed of sound propagating through the fluid or process mixture flowing within the process line 12 and determines the entrained air based on a measurement using the speed of sound, as will be described in greater detail hereinafter.

Similarly, the bleed line entrained air measurement module 18 includes a corresponding array of sensors 26 that measures the speed of sound propagating through the fluid or process mixture 11 flowing within the bleed line 16 and determines the bleed line entrained air based on a measurement using the speed of sound.

The bleed line 16 has a bleed valve 28 for bleeding the fluid or process mixture 11 into the bleed line 16. The bleed line 16 is re-coupled to the primary process line 12 via a boost pump 30 to recirculate the fluid or process mixture bled therefrom. The scope of the invention is not intended to be limited to the type or kind of bleed valve or boost pump used. The invention is shown and described in relation to a closed loop system; however, the scope of the invention is intended to include an open loop system in which the media from the bleed line is not returned to the process line.

The device 10 also includes a bleed line control module 32 for controlling the bleeding off of the portion of the fluid or process mixture from the process line via the bleed valve 28 and the reinjection of the same back to the process line 12 via the boost pump 30.

The modules 14, 18, 20, 22, 32 may be implemented using hardware, software, or a combination thereof. The scope of the invention is not intended to be limited to any particular implementation thereof. For example, a typical software implementation may include using a microprocessor architecture having a microprocessor, a random access memory (RAM), a read only memory (ROM), input/output devices and a control, address and databus for connecting the same.

Although the invention is described in relation to measuring or sensing entrained air in a fluid or process mixture using an array of sensors, the scope of the invention is intended to include other ways of measuring or sensing entrained air either known now or developed in the future. Moreover, although the invention is described in relation to using an array of sensors to determine the speed of sound, the scope of the invention is intended to include other ways of measuring the speed of sound either known now or developed in the future.

Entrained Gas Measurement

The present invention uses the speed at which sound propagates within a conduit to measure entrained air in slurries. This approach may be used with any technique that measures the sound speed of a fluid or process mixture. However, it is particularly synergistic with sonar based volumetric flow meters such as described in aforementioned U.S. patent application Ser. No. 10/007,736, now U.S. Pat. No. 6,889,562, in that the sound speed measurement, and thus gas volume fraction measurement, can be accomplished using the same hardware as that required for the volumetric flow measurement. It should be noted, however, that the gas volume fraction (GVF) measurement could be performed independently of a volumetric flow measurement, and would have utility as an important process measurement in isolation or in conjunction with other process measurements.

Firstly, the sound speed may be measured as described in aforementioned U.S. patent application Ser. No. 09/344,094, now U.S. Pat. No. 6,354,147, Ser. No. 10/007,749, now U.S. Pat. No. 6,732,575, U.S. patent application Ser. No. 10/349,716 filed Jan. 23, 2003 and/or U.S. patent application Ser. No. 10/376,427 filed Feb. 26, 2003, now U.S. Pat. No. 7,032,432 all incorporated herein by reference, using an array of unsteady pressure transducers. For a two component mixture, utilizing relations described in U.S. patent application Ser. No. 09/344,094, now U.S. Pat. No. 6,354,147, and/or Ser. No. 10/007,749, now U.S. Pat. No. 6,732,575, knowledge of the density and sound speed of the two components and the compliance properties of the conduit or pipe, the measured sound speed can be used to determine the volumetric phase fraction of the two components.

The sound speed of a mixture can be related to volumetric phase fraction ($\phi_i$) of the components and the sound speed (a) and densities ($\rho$) of the component through the Wood equation, where $$\frac{1}{\rho_{mix} a_{mix\infty}^2} = \sum_{i=1}^{N} \frac{\phi_i}{\rho_i a_i^2} \text{ where } \rho_{mix} = \sum_{i=1}^{N} \rho_i \phi_i$$

One dimensional compression waves propagating within a fluid contained within a conduit exert an unsteady internal pressure loading on the conduit. The degree to which the conduit displaces as a result of the unsteady pressure loading influences the speed of propagation of the compression wave. The relationship among the infinite domain speed of sound and density of a fluid; the elastic modulus (E), thickness (t), and radius (R) of a vacuum-backed cylindrical conduit; and the effective propagation velocity ($a_{eff}$) for one dimensional compression is given by the following expression:

$$ae_{ff} = \frac{1}{\sqrt{\frac{1}{a_{mix\infty}^2} + \rho_{mix} \frac{2R}{Et}}}$$

Note: "vacuum backed" as used herein refers to a situation in which the fluid surrounding the conduit externally has negligible acoustic impedance compared to that of the fluid internal to the pipe. For example, meter containing a typical water and pulp slurry immersed in air at standard atmospheric conditions satisfies this condition and can be considered "vacuum-backed".

For paper and pulp slurries, the conditions are such that for slurries with non-negligible amounts of entrained gas, say <0.01%, the compliance of standard industrial piping (Schedule 10 or 40 steel pipe) is typically negligible compared to that of the entrained air.

Figure 4:
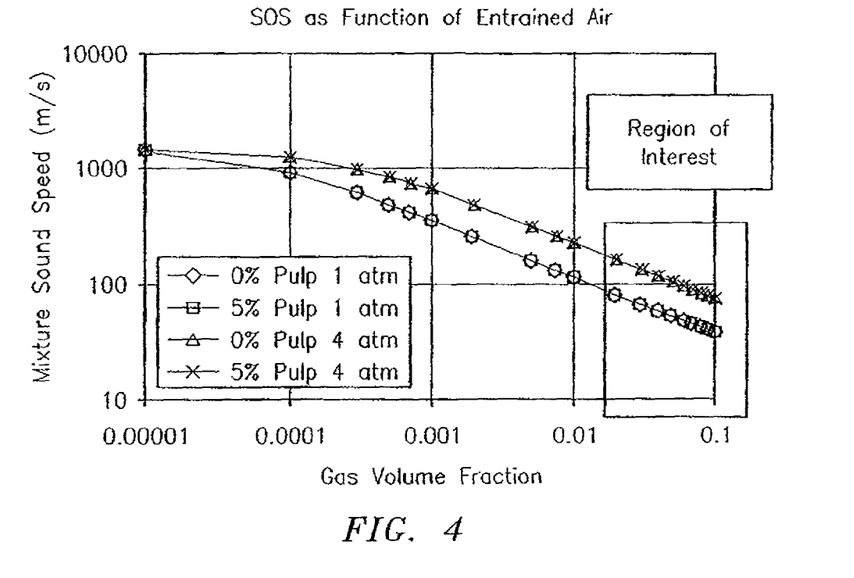
FIG. 4 is a graph of a gas volume fraction (GVF) between 0.00001 and 0.1 versus a mixture sound speed in meters per sec (m/s).
Figure 5:
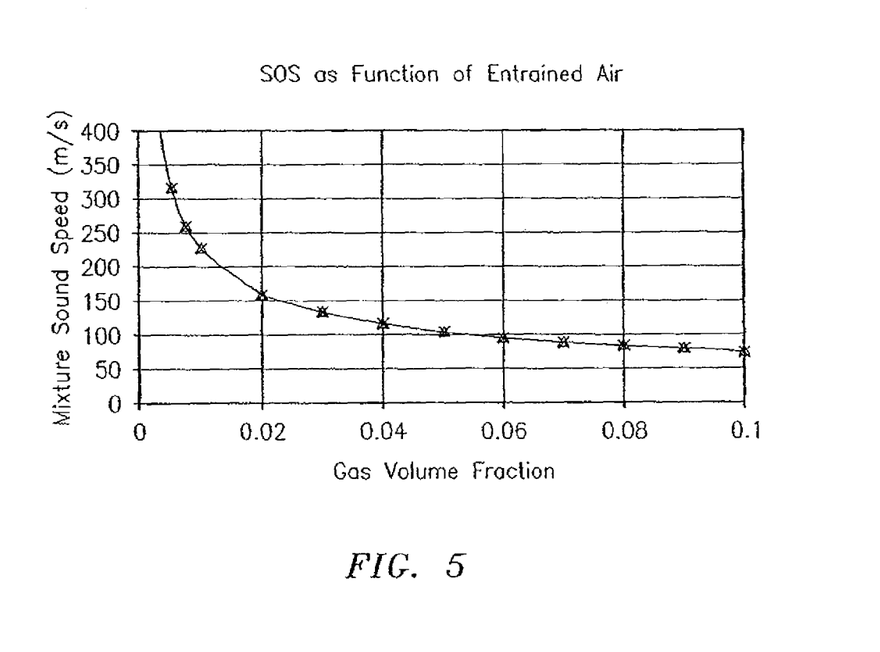
FIG. 5 is a graph of a gas volume fraction (GVF) between 0.0 and 0.1 versus a mixture sound speed in meters per sec.

FIGS. 4 and 5 show the relationship between sound speed and entrained air for slurries with pulp contents representative of the range used in the paper and pulp industry. Referring to FIG. 4, two slurry consistencies are shown; representing the lower limit, a pure water mixture is considered, and representing the higher end of consistencies, a 5% pulp/95% water slurry is considered. Since the effect of entrained air on the sound speed of the mixture is highly sensitive to the compressibility of the entrained air, the effect of the entrained air is examined at two pressures, one at ambient representing the lower limit of pressure, and one at four atmospheres representing a typical line pressure in a paper process. As shown, the consistency of the liquid slurry, i.e., the pulp content, has little effect on the relationship between entrained air volume fraction and mixture sound speed. This indicates that an entrained air measurement could be accurately performed, within 0.01% or so, with little or no knowledge of the consistency of the slurry. The chart does show a strong dependence on line pressure. Physically, this effect is linked to the compressibility of the air, and thus, this indicates that reasonable estimates of line pressure and temperature would be required to accurately interpret mixture sound speed in terms of entrained air gas volume fraction.

FIG. 4 also shows that for the region of interest, from roughly 1% entrained air to roughly 5% entrained air, mixture sound speeds ($a_{mix}$) are quite low compared to the liquid-only sound speeds. In the example shown above, the sound speed of the pure water and the 5% pulp slurry were calculated, based on reasonable estimates of the constituent densities and compressibilities, to be 1524 m/s and 1541 m/s, respectively. The sound speed of these mixtures with 1% to 5% entrained air at typical operating pressure (1 atm to 4 atms) are on the order of 100 m/sec. The implication of these low sound speeds is that the mixture sound speed could be accurately determined with an array of sensors, i.e. using the methodology described in aforementioned U.S. patent application Ser. No. 09/344,094, now U.S. Pat. No. 6,354,147, and/or Ser. No. 10/007,749, now U.S. Pat. No. 6,732,575, with an aperture that is similar, or identical, to an array of sensors that would be suitable to determine the convection velocity, using the methodology described in aforementioned U.S. patent application Ser. No. 10/007,736, now U.S. Pat. No. 6,889,562, which is incorporated herein by reference.

Figure 3:
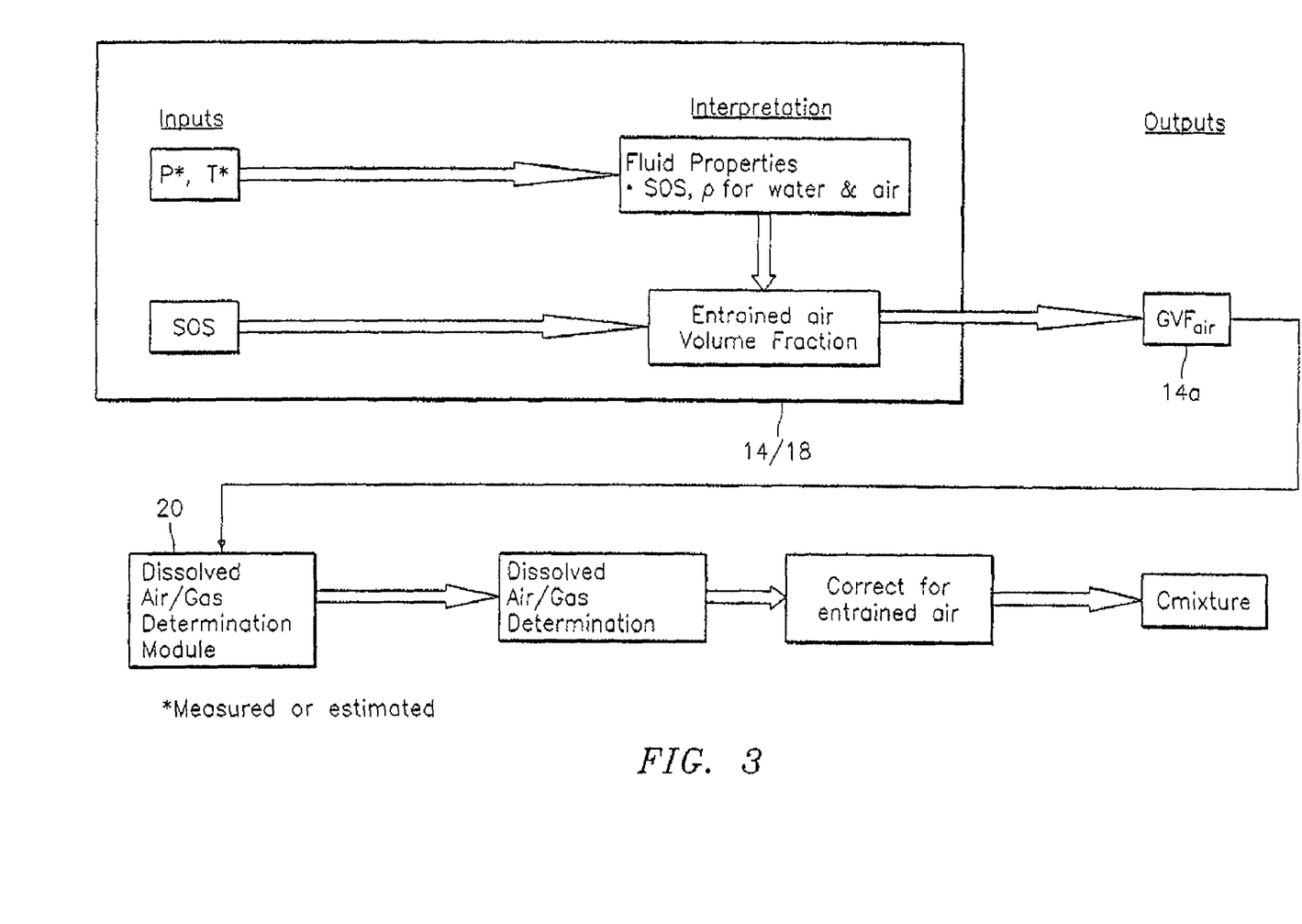
FIG. 3 is an overview of the system according to the present invention.

A flow chart of the proposed measurement is shown in FIG. 3, where the inputs are the mixture of SOS, P and T are pressure and temperature, respectively, and GVT air (gas volumetric flow of air) is provided from the box "Entrained Air Volume Fraction" as an output and to the box "correct for void fraction of air" and Q mixture (volumetric flow of the mixture) is provided from the box "Total Mixture Flow Rate" as an output and to the box "correct for void fraction of air".

Other information relating to the gas volume fraction in a fluid and the speed of sound (or sonic velocity) in the fluid, is described in "Fluid Mechanics and Measurements in two-phase flow Systems", Institution of mechanical engineers, proceedings 1969-1970 Vol. 184 part 3C, Sep. 24-25, 1969, Birdcage Walk, Westminster, London S. W. 1, England.

Based on the above discussion, one may use a short length scale aperture to measure the sound speed.

The characteristic acoustic length scale is: $\lambda = c/f$; where c is the speed of sound in a mixture, f is frequency and $\lambda$ is wavelength.

If Aperture=L and if $L/\lambda$ is approx. constant.

Then Lwater/$\lambda$water=Lwater*f/$C_{water} \approx L_{GVF}$*f/$c_{GVF}$

Therefore: $L_{GVF}$=Lwater($C_{GVF}/C_{water}$); where GVF is gas volume fraction.

Thus for SOS of water (Cwater=5,000 ft/sec), and SOS of the Gas volume fraction (C GVF=500 ft/sec) and a length aperture of L water=5 ft (which we have shown is sufficient to accurately measure the SOS of water), the length aperture for a gas volume fraction $L_{GVF}$ would be about 0.5 feet.

Note that this entrained air or gas volume fraction measurement GVFair may be used with any flow meter or consistency meter to correct for errors introduced into a measurement by entrained air. In particular, an electromagnetic flow meter will show an error when entrained air exists in the mixture. The present invention may be used to correct for this error. In addition, a consistency meter will show an error when entrained air exists in the mixture. The present invention may be used to correct for this error.

The scope of the invention is also intended to include using other models and corrections for determining entrained air in a fluid that may be used to compensate for gas volume fraction.

As shown in FIG. 3, the sonar meter measures the speed at which acoustic wave propagating in the process piping to determine the amount of entrained air in the process line. The acoustic wave can be generated by a pump or other device disposed in the piping system, or generated simply by the mixture/fluid flowing through the pipe, all of which provide a passive acoustic source. Alternatively, the sonar flow meter includes an active acoustic source that injects an acoustic wave into the flow such as by compressing, vibrating and/or tapping the pipe, to name a few examples.

e flow such as by compressing, vibrating and/or tapping the pipe, to name a few examples.

The connection between speed of sound of a two-phase mixture and phase fraction is well established for mixtures in which the wavelength of the sound is significantly larger than any inhomogenieities, i.e. bubbles, in the flow.

The mixing rule essentially states that the compressibility of a mixture $(1/(\rho a^2))$ is the volumetrically-weighted average of the compressibilities of the components. For gas/liquid mixtures at pressure and temperatures typical of paper and pulp industry, the compressibility of gas phase is orders of magnitudes greater than that of the liquid. Thus, the compressibility of the gas phase and the density of the liquid phase primarily determine mixture sound speed, and as such, it is necessary to have a good estimate of process pressure to interpret mixture sound speed in terms of volumetric fraction of entrained air. The effect of process pressure on the relationship between sound speed and entrained air volume fraction is shown in FIG. 4.

Conversely, however, detailed knowledge of the liquid/slurry is not required for entrained air measurement. Variations in liquid density and compressibility with changes in consistency have a negligible effect on mixture sound speed compared to the presence of entrained air. FIG. 5 shows the mixture sound speed as a function of entrained air volume fraction for two slurries, one with 0% wood fiber and the other with 5% wood fiber by volume. As shown, the relationship between mixture sound speed and gas volume fraction is essentially indistinguishable for the two slurries. Furthermore, mixture sound speed is shown to an excellent indicator of gas volume fraction, especially for the trace to moderate amounts of entrained air, from 0 to 5% by volume, typically encountered in the paper and pulp industry.

Speed of Sound Measurement

As mentioned earlier, the relationship between mixture sound speed and entrained air in bubbly liquids is well established. However, as will be developed below, in bubbly flows, these relations are only applicable for the propagation of relatively low frequency, long wavelength sound. While this restriction does not present any significant obstacles for the sonar meter, it does present significant challenges to ultrasonic sound speed measurement devices.

Ultrasonic meters typically operate in 100 Khz to several Mhz frequency range. For these meters, entrained air bubbles have length scales on the same order as the acoustic waves generated by the ultrasonic meters. They posed several problems. Firstly, the bubbles scatter the ultrasonic waves, impairing the ability of the ultrasonic meter to perform a sound speed measurement. Also, ultrasonic meters rely on information derived from only a small fraction of the cross sectional area of the pipe to be representative of the entire cross section, an assumption that breaks down for flows with inhomogenieties on the same length scale as the ultrasonic wavelength.

Sonar flow meters use an approach developed and commercialized specifically for multiphase flow measurement in the oil and gas industry. Sonar meters measure the propagation velocity of operationally generated sound in the ±100 to 1000 Hz frequency range. In this frequency range, sound propagates as a one-dimensional wave using the process pipe as a waveguide. The wavelength of sound in this frequency range (>1 m) is typically several orders of magnitude larger than the length scale of the any bubbles. The long wavelength acoustics propagate through the bubbles unimpeded, providing a robust and representative measure of the volumetrically averaged properties of the flow.

For the sound speed measurement, the sonar flow meter utilizes similar processing algorithms as those employed for the volumetric flow measurement. As with convective disturbances, the temporal and spatial frequency content of sound propagating within the process piping is related through a dispersion relationship.

$$k=\omega/a_{mix}$$

As before, k is the wave number, defined as $k=2\pi/\lambda$, $\omega$ is the temporal frequency in rad/sec, and $a_{mix}$ is the speed at which sound propagates within the process piping. Unlike disturbances which convect with the flow, however, sound generally propagates in both directions, with and against the mean flow. For these cases, the acoustic power is located along two acoustic ridges, one for the sound traveling with the flow at a speed of $a_{mix}+V_{mix}$ and one for the sound traveling against the flow at a speed of $a_{mix}-V_{mix}$.

Figure 6:
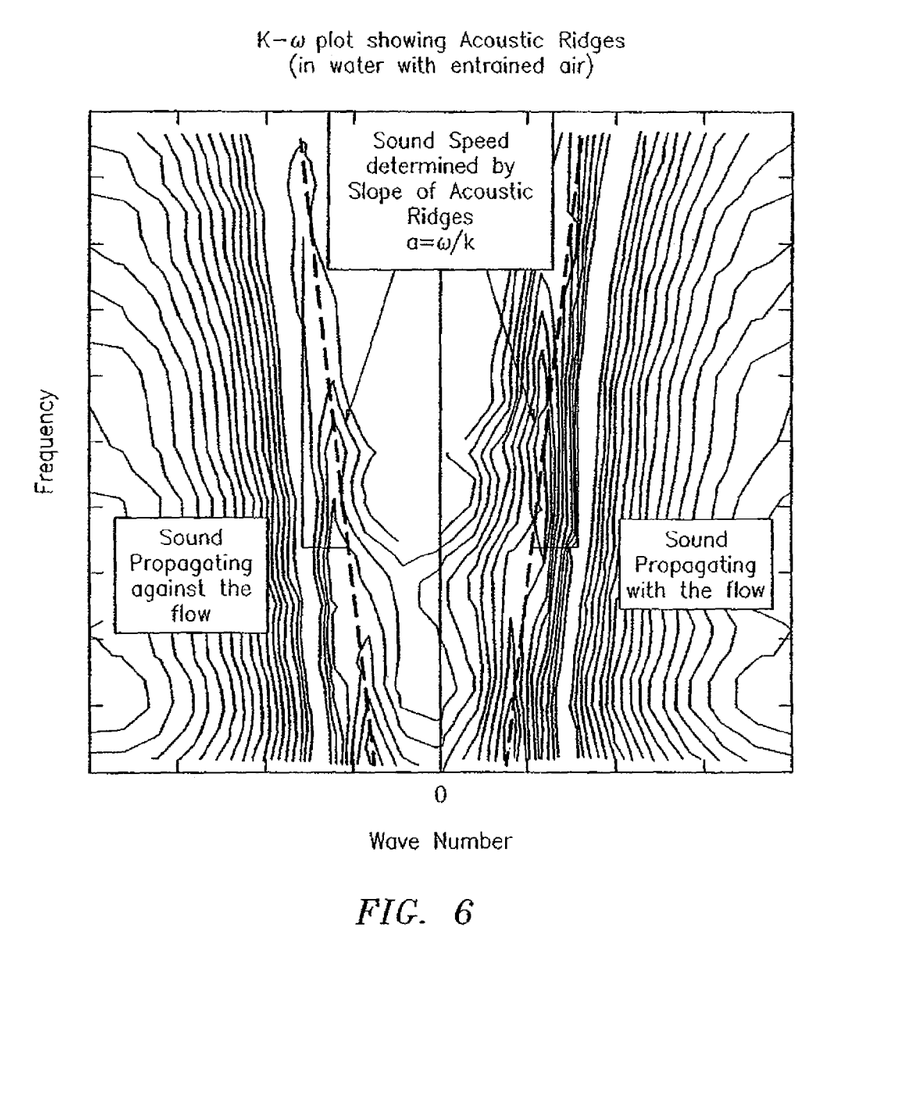
FIG. 6 is a k–ω plot constructed according to the present invention, showing acoustic ridges, wherein the fluid flowing in the pipe is water with entrained air.
Figure 7:
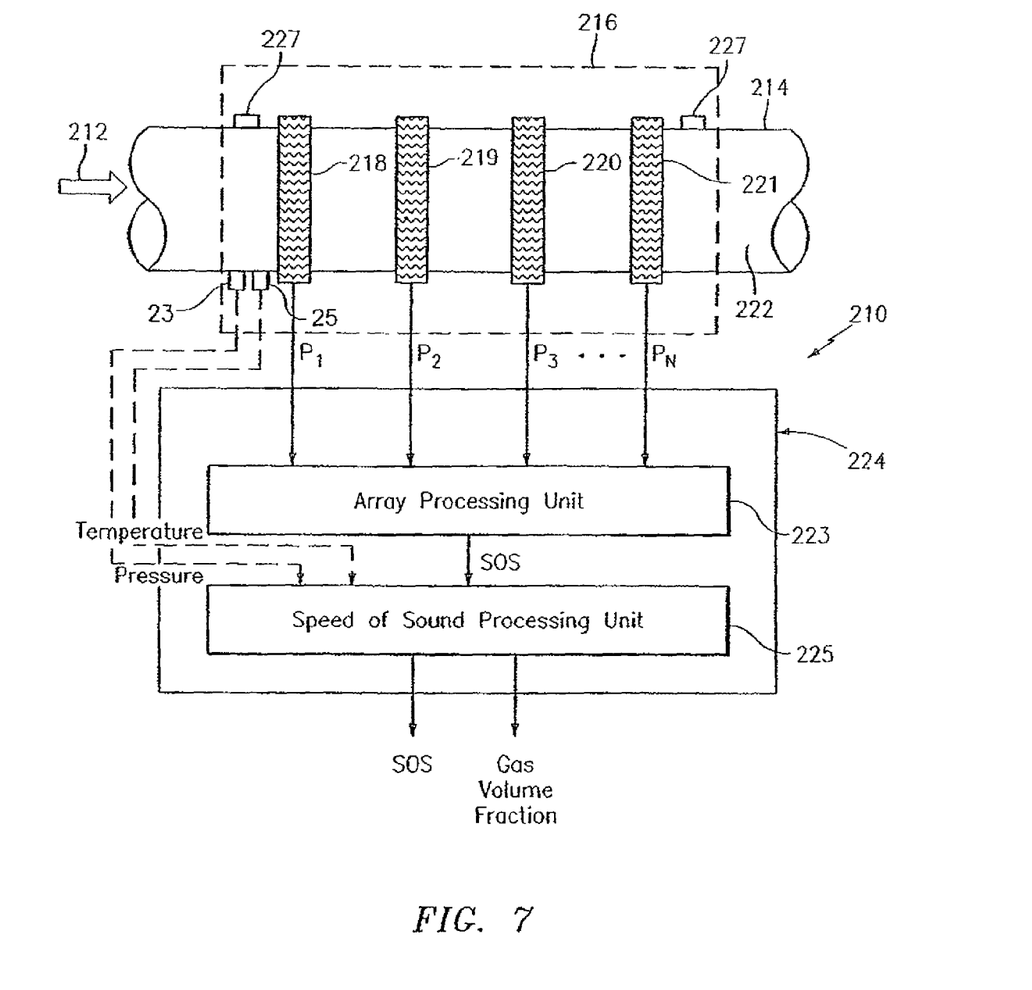
FIG. 7 is a block diagram of an apparatus for measuring entrained air in a fluid flowing within a pipe, such as a bleed line and primary process line, in accordance with the present invention.

FIG. 6 shows a k–ω plot generated for acoustic sound field recorded from water flowing at a rate of 240 gpm containing ~2% entrained air by volume in a 3 inch, schedule 10, stainless steel pipe. The k–ω plot was constructed using data from an array of strain-based sensors attached to the outside of the pipe. Two acoustic ridges are clearly evident. Based on the slopes of the acoustic ridges, the sound speed for this mixture was 330 ft/sec (100 m/s), consistent with that predicted by the Wood equation. Note that adding 2% air by volume reduces the sound speed of the bubbly mixture to less than 10% of the sound speed of single phase water. FIG. 7 illustrates a schematic drawing of one embodiment of the present invention. The apparatus 210 includes a sensing device 216 comprising an array of pressure sensors (or transducers) 218-221 spaced axially along the outer surface 222 of a pipe 214, having a process flow propagating therein, similar to that described hereinbefore. The pressure sensors measure the unsteady pressures produced by acoustical disturbances within the pipe, which are indicative of the SOS propagating through the mixture 212. The output signals ($P_1$-$P_N$) of the pressure sensors 218-221 are provided to the processor 224, which processes the pressure measurement data and determines the speed of sound, gas volume fraction (GVF) and other parameters of the flow as described hereinbefore.

In an embodiment of the present invention shown in FIG. 7, the apparatus 210 has a processing unit 224 having an array processing unit 223 and a speed of sound processing unit 225. The apparatus 210, similar to the arrays 24,26 of FIG. 2, also has the at least two pressure sensors 218-221 disposed axially along the pipe 214 for measuring the unsteady pressure $P_1$-$P_N$ of the mixture 212 flowing therethrough. The speed of sound propagating through the flow 212 is derived by interpreting the unsteady pressure field within the process piping 214 (e.g., the bleed line 16 and primary process line 12) using multiple transducers displaced axially over ~2 diameters in length. The flow measurements can be performed using ported pressure transducers or clamp-on, strain-based sensors. The apparatus 210 has the ability to measure the gas volume fraction and other parameters by determining the speed of sound of acoustical disturbances or sound waves propagating through the flow 212 using the array of pressure sensors 218-221.

Generally, the apparatus 210 measures unsteady pressures created by acoustical disturbances propagating through the flow 212 to determine the speed of sound (SOS) propagating through the flow. Knowing or measuring the pressure and/or temperature of the flow by a pressure sensor 23 and a temperature sensor 25, respectively, and the speed of sound of the acoustical disturbances, the processing unit 224 can determine the gas volume fraction of the mixture, similar to that shown in U.S. patent application Ser. No. 10/349,716, filed Jan. 21, 2003, now U.S. Publication 2003/0154036, U.S. patent application Ser. No. 10/376,427, filed Feb. 26, 2003, now U.S. Pat. No. 7,032,432, and U.S. Provisional Patent Application Ser. No. 60/528,802, filed Dec. 11, 2003 which are all incorporated herein by reference.

The apparatus 210 in FIG. 7 also contemplates providing one or more acoustic sources 227 to enable the measurement of the speed of sound propagating through the flow for instances of acoustically quiet flow. The acoustic sources may be disposed at the input end or output end of the array of sensors 218-221, or at both ends as shown. One should appreciate that in most instances the acoustics sources are not necessary and the apparatus passively detects the acoustic ridge provided in the flow 212. The passive noise includes noise generated by pumps, valves, motors, and the turbulent mixture itself.

Figure 8:
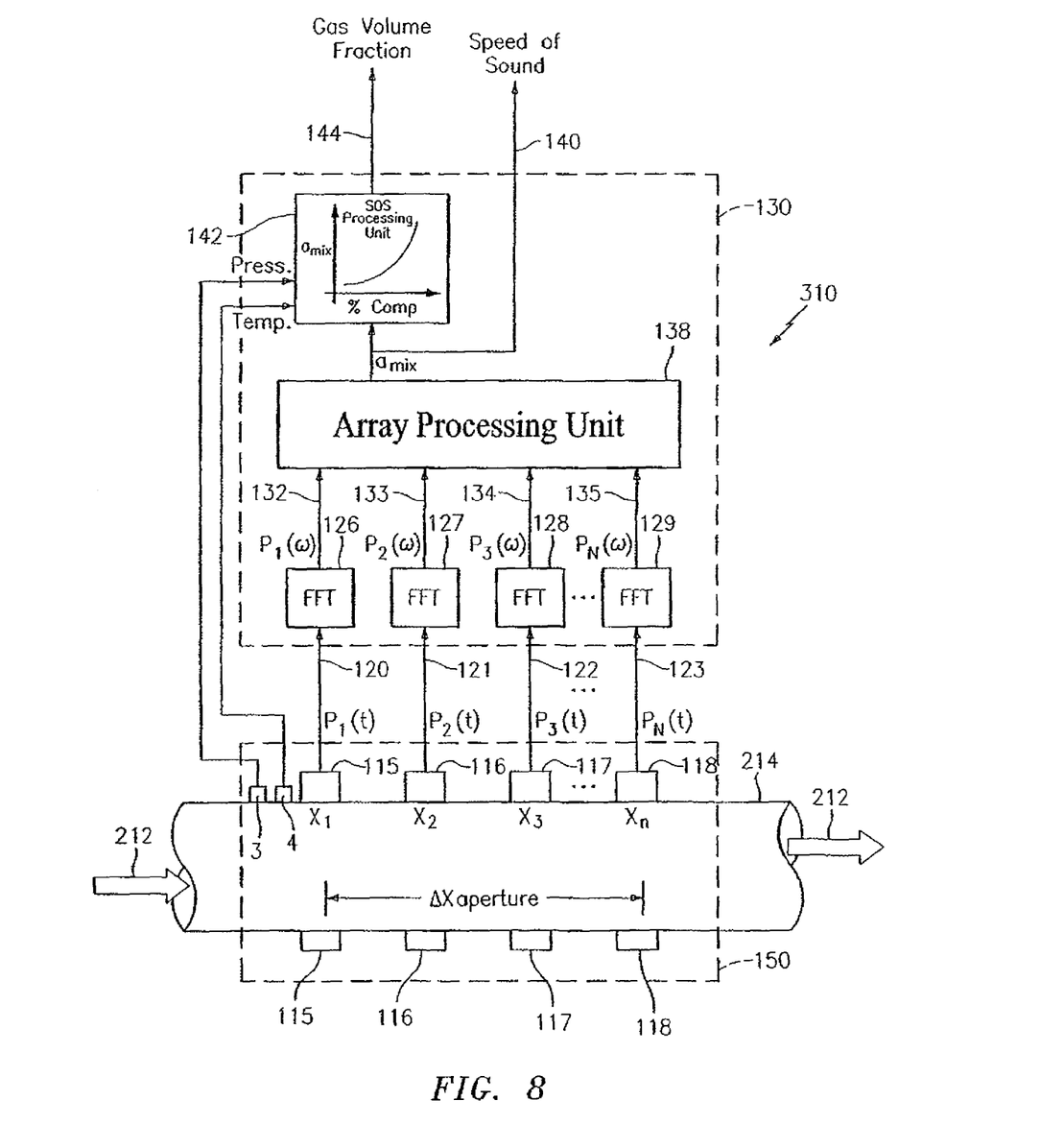
FIG. 8 is a block diagram of another embodiment of an apparatus for measuring entrained air in a fluid flowing within a pipe, such as a bleed line and primary process line, in accordance with the present invention.

The apparatus 210 of the present invention may be configured and programmed to measure and process the detected unsteady pressures $P_1(t)$-$P_N(t)$ created by acoustic waves propagating through the mixture to determine the SOS through the flow 212 in the pipe 214. One such apparatus 310 is shown in FIG. 8 that measures the speed of sound (SOS) of one-dimensional sound waves propagating through the mixture to determine the gas volume fraction of the mixture. It is known that sound propagates through various mediums at various speeds in such fields as SONAR and RADAR fields. The speed of sound propagating through the pipe and mixture 212 may be determined using a number of known techniques, such as those set forth in U.S. patent application Ser. No. 09/344,094, entitled "Fluid Parameter Measurement in Pipes Using Acoustic Pressures", filed Jun. 25, 1999, now U.S. Pat. No. 6,354,147; U.S. patent application Ser. No. 09/729,994, filed Dec. 4, 2002, now U.S. Pat. No. 6,609,069; U.S. patent application Ser. No. 09/997,221, filed Nov. 28, 2001, now U.S. Pat. No. 6,587,798; and U.S. patent application Ser. No. 10/007,749, entitled "Fluid Parameter Measurement in Pipes Using Acoustic Pressures", filed Nov. 7, 2001, now U.S. Pat. No. 6,732,575, each of which are incorporated herein by reference.

In accordance with one embodiment of the present invention, the speed of sound propagating through the mixture 212 is measured by passively listening to the flow with an array of unsteady pressure sensors to determine the speed at which one-dimensional compression waves propagate through the mixture 212 contained within the pipe 214.

As shown in FIG. 8, an apparatus 310 embodying the present invention has a sensing device 150 having an array of at least two acoustic pressure sensors 115,116, located at the locations $x_1,x_2$ axially along the pipe 214. One will appreciate that the sensor array may include more than two pressure sensors as depicted by pressure sensors 117,118 at locations $x_3,x_N$. The pressure generated by the acoustic waves may be measured through pressure sensors 115-118. The pressure sensors 115-118 provide pressure time-varying signals $P_1(t)$, $P_2(t),P_3(t),P_N(t)$ on lines 120,121,122,123 to a signal processing unit 130 to known Fast Fourier Transform (FFT) logics 126,127,128,129, respectively. The FFT logics 126-129 calculate the Fourier transform of the time-based input signals $P_1(t)$-$P_N(t)$ and provide complex frequency domain (or frequency based) signals $P_1(\omega),P_2(\omega),P_3(\omega),P_N(\omega)$ on lines 132, 133,134,135 indicative of the frequency content of the input signals. Instead of FFT's, any other technique for obtaining the frequency domain characteristics of the signals $P_1(t)$-$P_N(t)$, may be used. For example, the cross-spectral density and the power spectral density may be used to form a frequency domain transfer functions (or frequency response or ratios) discussed hereinafter.

The frequency signals $P_1(\omega)$-$P_N(\omega)$ are fed to an array processing unit 138, similar to the array processing unit 223, which provides a signal to line 140 indicative of the speed of sound of the mixture $a_{mix}$, discussed more hereinafter. The $a_{mix}$ signal, temperature signal (from temperature sensor 4), and pressure signal (from pressure sensor 3) is provided to an entrained gas processing unit 142, similar to the processing unit 225. The processing unit 142 converts $a_{mix}$ to a percent composition of a mixture and provides a gas volume fraction or % Comp signal to line 144 indicative thereof (as discussed hereinafter).

The data from the array of sensors 115-118 may be processed in any domain, including the frequency/spatial domain, the temporal/spatial domain, the temporal/wavenumber domain or the wave-number/frequency (k-ω) domain. As such, any known array processing technique in any of these or other related domains may be used if desired, similar to the techniques used in the fields of SONAR and RADAR.

One such technique of determining the speed of sound propagating through the flow 212 is using array processing techniques to define an acoustic ridge in the k-ω plane as shown in FIG. 6. The slope of the acoustic ridge is indicative of the speed of sound propagating through the flow 212. This technique is similar to that described in U.S. Pat. No. 6,587, 798 filed Nov. 28, 2001, titled "Method and System for Determining The Speed of Sound in a Fluid Within a Conduit", which is incorporated herein by reference. The speed of sound (SOS) is determined by applying sonar arraying processing techniques to determine the speed at which the one dimensional acoustic waves propagate past the axial array of unsteady pressure measurements distributed along the pipe 214.

The signal processor 224 performs a Fast Fourier Transform (FFT) of the time-based pressure signals $P_1(t)$-$P_N(t)$ to convert the pressure signal into the frequency domain. The power of the frequency-domain pressure signals are then determined and defined in the k-ω plane by using array processing algorithms (such as Capon and Music algorithms). The acoustic ridge in the k–ω plane, as shown in the k–ω plot of FIG. 6, is then determined The speed of sound (SOS) is determined by measuring slope of the acoustic ridge. The gas volume fraction is then calculated or otherwise determined, as described hereinafter.

The flow meter of the present invention uses known array processing techniques, in particular the Minimum Variance, Distortionless Response or other adaptive array processing techniques (MVDR, Music, or Capon technique), to identify pressure fluctuations, which convect with the materials flowing in a conduit and accurately ascertain the velocity, and thus the flow rate, of said material. These processing techniques utilize the covariance between multiple sensors 218-221 at a plurality of frequencies to identify signals that behave according to a given assumed model; in the case of the apparatus 310, a model, which represents pressure variations convecting at a constant speed across the pressure sensors comprising the sensing device 216.

Also, some or all of the functions within the processor 130 may be implemented in software (using a microprocessor or computer) and/or firmware, or may be implemented using analog and/or digital hardware, having sufficient memory, interfaces, and capacity to perform the functions described herein.

For certain types of pressure sensors, e.g., pipe strain sensors, accelerometers, velocity sensors or displacement sensors, discussed hereinafter, it may be desirable for the pipe 214 to exhibit a certain amount of pipe compliance.

The pressure sensors 218-221 described herein may be any type of pressure sensor, capable of measuring the unsteady (or ac or dynamic) pressures within a pipe, such as piezoelectric, optical, capacitive, resistive (e.g., Wheatstone bridge), accelerometers (or geophones), velocity measuring devices, displacement measuring devices, etc. If optical pressure sensors are used, the sensors 218-221 may be Bragg grating based pressure sensors, such as that described in U.S. patent application Ser. No. 08/925,598, entitled "High Sensitivity Fiber Optic Pressure Sensor For Use In Harsh Environments", filed Sep. 8, 1997, now U.S. Pat. No. 6,016,702, which are incorporated herein by reference. Alternatively, the sensors 218-221 may be electrical or optical strain gages attached to or embedded in the outer or inner wall of the pipe which measure pipe wall strain, including microphones, hydrophones, or any other sensor capable of measuring the unsteady pressures within the pipe 214. In an embodiment of the present invention that utilizes fiber optics as the pressure sensors 218-221, they may be connected individually or may be multiplexed along one or more optical fibers using wavelength division multiplexing (WDM), time division multiplexing (TDM), or any other optical multiplexing techniques.

For any of the embodiments described herein, the pressure sensors, including electrical strain gages, optical fibers and/or gratings among others as described herein, may be attached to the pipe by adhesive, glue, epoxy, tape or other suitable attachment means to ensure suitable contact between the sensor and the pipe 214. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe. If desired, for certain applications, the gratings may be detached from (or strain or acoustically isolated from) the pipe 212 if desired.

It is also within the scope of the present invention that any other strain sensing technique may be used to measure the variations in strain in the pipe, such as highly sensitive piezoelectric, electronic or electric, strain gages attached to or embedded in the pipe 214.

In certain embodiments of the present invention a piezoelectronic pressure transducer may be used as one or more of the pressure sensors 218-221 and it may measure the unsteady (or dynamic or ac) pressure variations inside the pipe 214 by measuring the pressure levels inside of the pipe 214. In an embodiment of the present invention the sensors 218-221 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

The pressure sensors 218-221 described herein may be any type of pressure sensor, capable of measuring the unsteady (or ac or dynamic) pressures within a pipe, such as piezoelectric, optical, thermal, capacitive, inductive, resistive (e.g., Wheatstone bridge), accelerometers (or geophones), velocity measuring devices, displacement measuring devices, etc. If optical pressure sensors are used, the sensors 218-221 may be Bragg grating based pressure sensors, such as that described in U.S. patent application Ser. No. 08/925,598, entitled "High Sensitivity Fiber Optic Pressure Sensor For Use In Harsh Environments", filed Sep. 8, 1997, now U.S. Pat. No. 6,016, 702. Alternatively, the sensors 218-221 may be electrical or optical strain gages attached to or embedded in the outer or inner wall of the pipe which measure pipe wall strain, including microphones, hydrophones, or any other sensor capable of measuring the unsteady pressures within the pipe 214. In an embodiment of the present invention that utilizes fiber optics as the pressure sensors 218-221, they may be connected individually or may be multiplexed along one or more optical fibers using wavelength division multiplexing (WDM), time division multiplexing (TDM), or any other optical multiplexing techniques.

A piezo-electronic pressure transducer may be used (or alternatively even a common strain gage may be used) as one or more of the pressure sensors 218-221, and it may measure the unsteady (or dynamic or ac) pressure variations Pin inside the pipe 214 by measuring the pressure levels (or for the strain gage, the elastic expansion and contraction of the diameter of the pipe 214. In an embodiment of the present invention the sensors 218-221 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

For any of the embodiments described herein, the pressure sensors, including electrical strain gages, optical fibers and/or gratings among others as described herein, may be attached to the pipe by adhesive, glue, epoxy, tape or other suitable attachment means to ensure suitable contact between the sensor and the pipe 212. The sensors may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe. If desired, for certain applications, the gratings may be detached from (or strain or acoustically isolated from) the pipe 212 if desired.

It is also within the scope of the present invention that any other strain sensing technique may be used to measure the variations in strain in the pipe, such as highly sensitive piezo-electric, electronic or electric, strain gages attached to or embedded in the pipe 212.

While the sonar-based flow meter using an array of sensors to measure the speed of sound of an acoustic wave propagating through the mixture, one will appreciate that any means for measuring the speed of sound of the acoustic wave may used to determine the entrained air volume fraction of the mixture/fluid.

It should be understood that, unless stated otherwise herein, any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein without departing from the spirit and scope of the present invention.

What is claimed is:

1. An apparatus for determining dissolved air/gas in a fluid or process mixture passing through a primary process line, comprising:
    one or more modules configured to respond to a first signal containing information about a sensed air/gas dissolved in a primary process line, and configured to respond to a second signal containing information about a sensed air/gas dissolved in a bleed line coupled to the primary process line for bleeding the fluid or process mixture, where the sensed air/gas dissolved in the primary process line and the sensed air/gas dissolved in the bleed line are measured based on the speed of sound propagating through the fluid or process mixture; and configured to provide a third signal containing information about the dissolved air/gas in the fluid or process mixture passing through the primary process line based at least partly on the information contained in the first signal and second signal.

2. An apparatus according to claim 1, wherein the information in the third signal is based at least partly on a difference between the sensed entrained air/gas in the primary process line and the sensed entrained air/gas in the bleed line.

3. An apparatus according to claim 1, wherein the pressure in the bleed line is lower than the pressure in the primary process line.

4. An apparatus according to claim 1, wherein
    the apparatus further comprises a primary process line entrained air measurement module, and the one or more modules is configured to receive the first signal from the primary process line entrained air measurement module; and
    the apparatus further comprises a bleed line entrained air measurement module, and the one or more modules is configured to receive the second signal from the bleed line entrained air measurement module,
    where either the primary process line entrained air measurement module, the bleed line entrained air measurement module, or both, is configured to include an array of sensors that measures the speed of sound propagating through the fluid or process mixture flowing within either the primary process line, the bleed line, or both, and determines entrained air/gas based at least partly on a measurement using the speed of sound.

5. An apparatus according to claim 1, wherein the apparatus comprises a dissolved air determination processor module, and the third signal is received from the dissolved air determination processor module.

6. An apparatus according to claim 1, wherein the bleed line is re-coupled to the primary process line to recirculate the portion of the fluid or process mixture bled from the bleed line.

7. An apparatus according to claim 1, wherein the portion of the fluid or process mixture from the primary process line is bled off either continuously or periodically.

* * * * *